United States Patent [19]

Schwartz et al.

[11] Patent Number: 5,607,463
[45] Date of Patent: Mar. 4, 1997

[54] INTRAVASCULAR MEDICAL DEVICE

[75] Inventors: Robert S. Schwartz, Rochester; Ronald G. Tuch, Plymouth; Rodney G. Wolff, Minnetonka, all of Minn.

[73] Assignee: Medtronic, Inc., Minneapolis, Minn.

[21] Appl. No.: 40,045

[22] Filed: Mar. 30, 1993

[51] Int. Cl.⁶ .................. A61F 2/06; A61F 2/04
[52] U.S. Cl. ........................... 623/1; 623/12
[58] Field of Search .................... 623/1, 11, 12; 606/191–200; 600/36; 604/93

[56] References Cited

U.S. PATENT DOCUMENTS

| | | |
|---|---|---|
| 3,690,325 | 9/1972 | Kenney . |
| 3,718,142 | 2/1973 | Mulier . |
| 3,797,485 | 3/1974 | Urquhart ........................... 604/93 |
| 3,939,834 | 2/1976 | McMahon . |
| 4,405,319 | 9/1983 | Cosentino . |
| 4,601,724 | 7/1986 | Hooven . |
| 4,612,100 | 9/1986 | Edeling . |
| 4,718,905 | 1/1988 | Freeman . |
| 4,860,446 | 8/1989 | Lessar . |
| 4,871,366 | 10/1989 | von Recum et al. ............... 623/1 |
| 5,016,808 | 5/1991 | Heil, Jr. . |
| 5,074,313 | 12/1991 | Dahl . |
| 5,118,400 | 6/1992 | Wollam . |
| 5,152,783 | 10/1992 | Suzuki . |
| 5,226,909 | 7/1993 | Evans et al. ....................... 604/22 |
| 5,282,861 | 2/1994 | Kaplan ............................... 623/11 |

Primary Examiner—Debra S. Brittingham
Attorney, Agent, or Firm—Daniel W. Latham; Harold R. Patton

[57] ABSTRACT

An indwelling intravascular device having at least one tissue-contacting surface in which the tissue-contacting surface is provided with improved tissue compatibility by applying to the base material comprising the tissue-contacting surface a thin layer of a tissue-compatible metal. Metals from Group VA of the Periodic Table are preferred. The metal layer is particularly useful in vascular prosthetic devices such as vascular grafts and stents.

13 Claims, 2 Drawing Sheets

INTRAVASCULAR MEDICAL DEVICE

BACKGROUND OF THE INVENTION

This invention relates to indwelling intravascular medical devices with improved compatibility with the intravascular environment. It particularly relates to intravascular prosthetic devices such as vascular grafts, vascular patches, or stents used to repair injured or defective blood vessels.

Medical devices which serve as indwelling intravascular devices such as vascular prostheses, catheters and the like are well known. However, the use of such biomaterials in medical devices can stimulate adverse body responses, including rapid thrombogenic action and inflammatory tissue reactions. Thus, both blood and tissue can be affected by the presence of such materials. For blood compatibility, it is well known that various plasma proteins play a role in initiating platelet and fibrin deposition on device surfaces. However, there is no single theory which explains why one material will prove to be exceptionally compatible with blood while another is not. A protein can adsorb to different material surfaces by different methods due to the wide variety of functional groups on the exterior of all proteins. Notwithstanding the lack of a theoretical basis to predict blood compatibility, tests have shown that some materials are particularly susceptible to thrombosis while other materials have been found to be exceptionally compatible with blood in intravascular applications.

Similarly, tissue reactions with medical devices are known to be important but are not well understood. The capacity of the natural endothelial cell lining of a blood vessel to regenerate, resist thrombosis and to resist bacterial invasion is well known. It is therefore desirable when using indwelling intravascular medical devices to maintain the existing endothelial cell layer and to extend the endothelial cell layer to cover the blood-contacting portion of the device surface. The response of the body to vascular graft materials, for example, can be to form a pseudointima, a surface lining of fibrin and entrapped blood-born cells on the graft; or to form a neointima, an endothelial cell monolayer covering the graft with or without the presence of an underlying structure of fibroblasts or smooth muscle cells. One adverse consequence of neointimal growth can be the development of neointimal fibrous hyperplasia, exuberant tissue growth within the neointima or within the natural vessel tissue at the anastomosis which can threaten blood vessel closure (especially in small blood vessels such as those having a diameter of only 3–4 mm). It is therefore desired that such hyperplasia be suppressed following the implantation of a medical device.

Materials to be used in vascular prostheses such as vascular grafts, vascular patches and stents are therefore particularly demanding in terms of blood compatibility and tissue compatibility since they are intended to be permanently affixed in the blood vessel and since they are typically applied at the site of a blood vessel injury that would be expected to trigger thrombosis and rapid cell growth as a normal part of the body's healing mechanism.

A "biomaterial" may be defined as a material that is substantially insoluble in body fluids and that is designed and constructed to be placed in or onto the body or to contact fluid of the body. Ideally, a biomaterial will not induce undesirable reactions in the body such as blood clotting, tissue death, tumor formation, allergic reaction, foreign body reaction (rejection) or inflammatory reaction; will have the physical properties such as strength, elasticity, permeability and flexibility required to function for the intended purpose; can be purified, fabricated and sterilized easily; will substantially maintain its physical properties and function during the time that it remains implanted in or in contact with the body.

An extensive program of testing was conducted for candidate polymeric biomaterials to determine their suitability for use in indwelling intravascular applications such as in vascular prostheses. In those tests, a stent was covered on only one side with a candidate polymer. The stent was then delivered on a balloon transluminally into a coronary blood vessel of a live pig having a diameter of approximately 3–4 mm where the stent was expanded to bring the candidate material into contact with the blood vessel to an extent similar to what may occur in a conventional percutaneous transluminal coronary angioplasty (PTCA) procedure. After a predetermined interval, the blood vessel containing the test stent was sectioned and the portion of the vessel in contact with the polymeric material was visually compared to the portion of the blood vessel that received no contact in order to determine the response of the blood vessel to the polymeric material. To date, few, if any, polymers have been found to be promising for small vessel intravascular applications due to adverse reactions with blood and/or the vascular tissue.

One approach to improved biocompatibility for biomaterials in particular applications is to modify only the surface of the biomaterial so that the bulk properties of the biomaterial are preserved while the surface characteristics are changed to provide a more favorable biological response from the body of the person in which it is implanted. One way to do this is to attach various "biomolecules" which can promote the attachment and growth of a normal cell layer such that the body accepts the cell-attached device as a normal part of the body. Biomolecules such as growth factors and cell attachment proteins which have been attached to the device surface could be used for this purpose. In addition, biomolecules such as antithrombogenics, antiplatelets, anti-inflammatories and the like have also been used to improve the biocompatibility of surfaces.

An example of another material modification approach can be found in U.S. Pat. No. 4,718,905 issued to Freeman in which the haptic loop elements of an intraocular lens are treated with ion beam implantation methods (preferably introducing nitrogen into the polypropylene material of the haptic loops) to make the loops more resistant to degradation by body fluids over time.

It is therefore an object of the present invention to provide an indwelling intravascular device which has a tissue-contacting and blood-contacting surface of improved biocompatibility.

It is also an object of the present invention to provide such an improved indwelling intravascular device in which the bulk properties of the base biomaterial are substantially unaffected.

It is yet another object of the present invention to provide a method for making such an improved indwelling intravascular device.

SUMMARY OF THE INVENTION

These and other objects are accomplished by the present invention. We have discovered that in an indwelling intravascular device having at least one tissue-contacting surface, that the tissue-contacting surface can be provided with improved compatibility for the blood vessel by applying to the base material comprising the tissue-contacting surface a thin layer of a metal from Group VB of the Periodic Table in a manner that causes the metal to be strongly adherent to the base material. Of the metals of this group, tantalum and niobium are preferred. This metal surface layer is particularly useful for polymeric surfaces which would otherwise produce thrombotic or inflammatory responses when used in implanted intravascular devices and especially useful for elastomers which are required to flex in the intravascular application since the coating is sufficiently thin to enable the elastomer to flex normally. To accomplish this, the metal layer is less than about 3000 angstroms thick and preferably less than about 1000 angstroms thick. Thus, indwelling intravascular devices such as a vascular prosthesis, an artificial heart valve, an electrical lead, or a catheter can be provided with enhanced biocompatibility with the present invention.

In one aspect of the invention, the device is a vascular prosthesis such as an intravascular stent, a vascular graft or a vascular patch used to repair injured or defective blood vessels. In such devices, both the blood-contacting and tissue-contacting surfaces can be furnished with the metal layer according to the invention. Thus, on the side of the device past which blood flows, excessive clotting and subsequent neointimal overgrowth is inhibited and blood flow through the vessel is not impeded by such growth and, on the lumen-contacting side of the device where the device may contact injured endothelial and smooth muscle tissue, the metal layer will reduce the tendency toward inflammatory response and subsequent neointimal cell hyperplasia which would also tend to promote closure or restenosis of the injured blood vessel as well as general loss of vessel wall architecture.

In yet another aspect of the invention, the properties of a blood-compatible or tissue-compatible metal layer can be of particular use in intravascular stents which are introduced transluminally to a desired location in a blood vessel and then expanded radially (e.g. by a balloon on a PTCA catheter) into contact with the blood vessel wall. Since the metal layer can be made so very thin, when it is applied to an intravascular stent, it will not tend to restrict the intended radial expansion of the device. For example, a stent can be provided from a hollow, cylindrical elastomeric film supported by a framework of a ductile metal (or, alternatively, for a self-expanding stent, a framework of a resilient, springy metal). The elastomeric film can be provided with a thin layer of a blood or tissue-compatible metal, preferably on both the blood-contacting inner surface of the cylindrical device and the lumen-contacting outer surface of the cylindrical device. Blood and tissue-compatible metals that can be used include, for example, gold, platinum, tantalum, niobium and the like. Preferably, for the tissue- contacting surfaces, a 360 degree coverage of the metal layer should be employed to prevent any contact between the tissue of the vessel lumen and the polymeric base material. The stent can then be crimped onto a balloon of a PTCA catheter, delivered transluminally to the site of the blood vessel injury or defect and expanded into contact with the native blood vessel without experiencing significant resistance to expansion from the applied metal layer. The delivery catheter can then be removed, leaving the stent of the present invention in the blood vessel. If desired, the base material can be a polymer that acts as a carrier for therapeutic substances which may tend to inhibit restenosis and the metal layer can be perforated at selected locations on the lumen-contacting outer surface in order to allow the therapeutic substance to elute from the base material. Preferably, the perforations would be quite small to prevent cells, such as red blood cells, from making contact with the base material. Also, in order to provide additional resistance to thrombosis, the blood-contacting surface of the stent could be further modified by applying an anti-thrombotic material as a coating over the thin metal layer. Thus, for example, heparin could be coated onto the metal layer or attached to the metal layer by methods which are well known to those skilled in the art.

The preferred method for making the indwelling intravascular device of the present invention is to first provide a base material for the blood-contacting or tissue-contacting surface in the desired shape and then apply to the base material the thin, adherent layer of metal by physical vapor deposition. Physical vapor deposition (PVD) processes include processes in which a thin film of metal can be applied to a surface by physical techniques such as vacuum deposition, ion plating, and sputtering. In a vascular prosthesis where the base material is a flexible polymeric film or a flexible mat of woven filaments in a hollow, cylindrical shape, both the inner and outer surfaces of the prosthesis can have a layer of metal applied by PVD by applying the metal layer to the outside surface and then simply everting the device (i.e. turning the cylindrical base material inside out to bring the outside surface to the inside and the inside surface to the outside) and then applying the metal layer to the new outer surface.

DETAILED DESCRIPTION OF THE INVENTION

Figure 1:
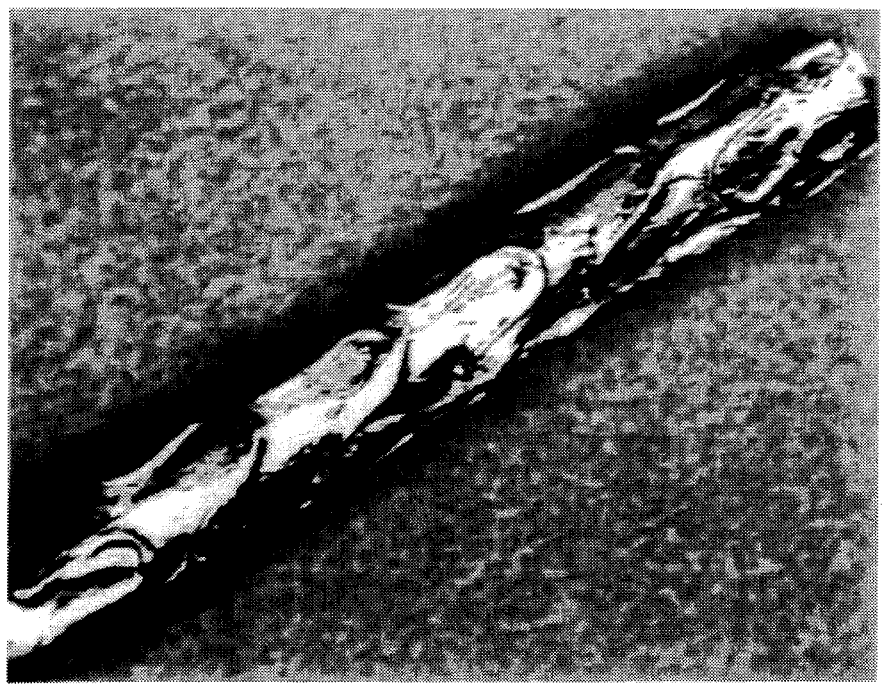
FIG. 1 is a photograph showing a side view of a stent having a thin layer of applied metal according to the present invention.

The indwelling intravascular device of the present invention includes devices which are intended for implantation in the vascular system for an extended period and which includes at least one tissue-contacting surface which may cause a vascular injury or provoke an adverse tissue response due to contact with the blood vessel wall. Thus devices such as vascular prostheses (e.g. vascular grafts, intravascular stents, vascular patches or heart valves) which are intended to repair or replace injured or defective blood vessels could be indwelling intravascular devices according to the present invention. Also intravascular catheters and catheter-like devices (e.g. heart pacemaker leads, intravascular pumping devices) which are intended as permanent or semi-permanent implants could be indwelling intravascular devices according to the present invention. Also, intravascular sensors for measuring pressure, oxygen content, and the like could be indwelling intravascular devices according to the present invention. It is well known to those skilled in the art that these devices contain tissue-contacting surfaces which may raise concerns about tissue injury and healing responses.

The base material for the tissue-contacting surface can be any of a wide variety of materials including suitable metals such as titanium or stainless steel or a suitable polymer such as polyolefins, such as, polyethylene and polypropylene, polyisobutylene and ethylene-alphaolefin copolymers; silicone polymers such as polydimethylsiloxane; acrylic polymers and copolymers, such as polyacrylate, polymethylmethacrylate, polyethylacrylate; vinyl halide polymers and copolymers, such as polyvinyl chloride; fluoropolymers such as polytetrafluoroethylene, chlorotrifluoroethylene, and fluorinated ethylene-propylene; polyvinyl ethers, such as polyvinyl methyl ether; polyvinylidene halides, such as polyvinylidene fluoride and polyvinylidene chloride; polyacrylonitrile, polyvinyl ketones; polyvinyl aromatics, such as polystyrene, polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; natural and synthetic rubbers, including butadiene-styrene copolymers, poly-isoprene, synthetic polyisoprene, polybutadiene, butadiene-acrylonitrile copolymers, polychloroprene rubbers, polyisobutylene rubber, ethylene-propylenediene rubbers, isobutylene-isoprene copolymers and polyurethane rubbers; polyamides, such as Nylon 66 and polycaprolactam; polyesters such as polyethylene terephthalate, alkyd resins; phenol-formaldehyde resins; urea-formaldehyde resins, melamine-formaldehyde resins; polycarbonates; polyoxymethylenes; polyimides; polyethers; epoxy resins, polyurethanes; wool; cotton; silk; rayon; rayon-triacetate; cellulose, cellulose acetate, cellulose butyrate; cellulose acetate butyrate; cellophane; cellulose nitrate; cellulose propionate; cellulose ethers; and carboxymethyl cellulose; minerals or ceramics such as glass or hydroxyapatite; organic materials such as cellulose and compressed carbon; and other natural and synthetic materials. Among the polymeric materials, the most desirable materials are those with established uses in intravascular medical devices such as silicone rubbers, polyurethanes, polyesters, fluoropolymers and polyolefins.

The metal layer is superimposed over the base material in a thin layer in order to provide a substitute surface of improved biocompatibility when in contact with vascular tissue. The tissue-compatible metal employed is preferably a metal from Group VB of the Periodic table of the elements. This group includes vanadium, niobium and tantalum. Tantalum and niobium are preferred in the present invention and tantalum is the most preferred metal. The metal is superimposed on the base material in a very thin layer. The metal layer is only required to be very thin since the purpose of the metal layer is to change the surface chemistry of the base material so that it will interface with tissue in the vascular lumen without causing adverse tissue reactions. Preferably, the layer is less than about 3000 angstroms thick and most preferably less than about 1000 angstroms thick so that the mechanical properties of the base material are not materially affected during the operation of the device by the presence of the metal layer. The layer is also tightly adhered to the base material to prevent the metal layer from being separated from the base material while the intravascular device is in the vascular lumen.

One family of methods employed to produce such coatings is sometimes referred to as physical vapor deposition (PVD). The PVD methods include vacuum deposition, sputter deposition and ion plating. Metalized layers such as those provided by PVD are well known by those skilled in the art and are preferably used in the present invention. The advantages of a PVD metal layer is there are no significant dimensional changes in the base material and there is a reduced possibility that the metal surface will peel off or delaminate. PVD processes are also typically low temperature processes suitable for use with temperature-sensitive medical device components and are also highly controllable and easily reproducible. The following is a general description of these methods as they are known to those skilled in the physical vapor deposition art.

In vacuum deposition, the desired coating metal is transferred to the vapor state by a thermal or ballistic process at low pressure. The vapor is expanded into the vacuum toward the surface of the precleaned base material. Diffusion-limited transport and gas-phase prenucleation of the coating material is avoided by processing entirely in a vacuum that is sufficiently low to ensure that most of the evaporated atoms arrive at the base material without significant collisions with background gas. At the base material, the arriving atoms of coating metal are condensed to a solid phase. The condensation process involves surface migration, nucleation of crystals, growth of crystals to impingement, and often renucleation. In this process, the energy of the physically evaporated atom usually is fractions of an electron volt, depending on the physical properties of the coating material, i.e., melting point.

In sputtering, the coating material is maintained in a solid form and then suitably bombarded by positive ions of an inert gas generated by a glow discharge or other ion source. The coating material or target generally is negatively biased by several hundred to a few thousand volts. The high velocity ions that impinge on the coating material dislodge surface atoms by sputtering. Sputtered atoms are ejected from the coating metal surface with energies of typically between one and ten electron volts. Sputtering usually is carried out in an inert gas at a pressure which allows a glow discharge to be supported by electron impact which provides a source of ions to maintain a steady-state process. Alternatively, the coating material first can be evaporated or sputtered to vapor and then partially converted to the ionized state by electron bombardment.

Ion plating is conducted with either evaporation or sputtering of the metal to provide a deposit of metal on a base material which is maintained at a negative potential. The ionized portion of the vapor cloud can be accelerated to high energies, e.g., a few thousand electron volts, by maintaining the negative bias on the base material so that the ions impact on the base material. The result of this surface activity is greatly improved coating adherence, uniformity, and the ability to deposit a substantial fraction of the deposited metal on the surfaces not in line-of-sight with the source. If the accelerating voltages are higher, e.g., 80–100 kV, the ions become permanently embedded as atoms in the base material and the process is ion implantation. At these energies, the ions chemically alter the near-surface region of the material. The properties of the near surface may be drastically changed by this internal alloying of the base material.

In the present invention, the physical vapor deposition method selected will depend on the properties of the base material and the metal layer to be provided since the character of the bond between the metal layer and the base material depends upon the particular metal and the base material. It may be a chemical or metallic bond or a van der Waals interaction. Where adhesion of the metal layer to the base material is difficult to achieve, physical vapor deposition variants employing higher ion energies may be required.

In a preferred embodiment of the invention, the indwelling intravascular device is a vascular prosthesis such as an intravascular stent, a vascular graft or a vascular patch. These are typically used to repair injured or defective blood vessels. In such devices, both the blood-contacting and lumen-contacting surfaces can be furnished with a thin metal layer. Thus, on the inward facing, blood-contacting side of the device, the potential for excessive thrombosis and proliferative neointimal overgrowth is reduced and, on the outer, lumen-contacting side of the device where the device may contact injured tissue, the metal layer will reduce the tendency toward neointimal cell hyperplasia and inflammatory response which would otherwise tend to promote closure or restenosis of the injured blood vessel as well as loss of the vessel wall architecture.

The metal layer can be of particular use in intravascular stents which are introduced transluminally to a desired location in a blood vessel and then expanded radially (e.g. by a balloon on a PTCA catheter) into contact with the blood vessel wall. Since the metal layer is so very thin, when it is applied to an intravascular stent, it will not tend to restrict the intended radial expansion of the device. For example, a stent can be provided from a hollow, cylindrical elastomeric film supported by a framework of a ductile metal. A suitable framework of ductile metal could be as disclosed in U.S. Pat. No. 4,886,062 issued to Wiktor which is incorporated herein by reference in its entirety. In the Wiktor patent, a generally helical wire winding provides a hollow, cylindrical shape which could be used as a supporting structure for a thin polymeric film of a (e.g. silicone or polyurethane) biostable elastomer. The elastomeric film can be provided with a thin metal layer of a tissue and/or blood-compatible metal, preferably on both the blood contacting inner surface of the cylindrical device and the lumen-contacting outer surface of the cylindrical device. This can be accomplished for an elastomeric film by making the film into a cylindrical shape; depositing a tissue and/or blood-compatible metal layer (e.g. tantalum, niobium, gold, or platinum) on the outside surface of the film cylinder; everting the cylinder so that the metal layer is on the inside; attaching the wire supporting structure to the outside surface of the everted cylinder; and depositing a metal layer on the outside surface of the everted cylinder. The wire supporting structure could also be placed inside the film cylinder which would allow the film cylinder to be pressed into contact with the wall of the blood vessel by the supporting structure or the wire supporting structure could be secured over the outside of the film by an adhesive. If an adhesive is used, the adhesive could also include therapeutic substances which would elute at the lumen wall. Thus, antiplatelet agents, anticoagulant agents, antimicrobial agents, antimetabolic agents, anti-inflammatory agents and other drugs could be supplied at the vessel wall to reduce the incidence of restenosis. Also, if an adhesive is used, the adhesive bond between the film cylinder and the wire supporting structure may be made before the metal layer is applied since the adhesive may bond to the substrate material better than to the metal layer. The metal layer could then be applied over the adhesive.

Since the thin metal layer may develop micro-cracks that may separate as the stent is expanded, it is preferred that the a polymeric base material be made to fit somewhat loosely around the balloon on which it is delivered in order to prevent excessive stretching when the stent is expanded into contact with the blood vessel. For example, for a stent made for use in a coronary artery, a polymeric base material may be made about 2.5 mm in diameter and assembled into a stent which is then crimped onto a balloon at a diameter of about 1.5 mm. The resulting stent can then be expanded up to a diameter of about 4.0 mm without difficulty.

It has been noted for stent applications that higher energy PVD methods such as ion plating or sputtering at higher voltages may be preferred due to the improved adhesion of the metal to the surface of a polymer that is subject to significant deformation at the time of delivery into the blood vessel. For example, stent samples sputtered at 1000 volts have exhibited delamination in vivo after 30 days implantation while one stent sample sputtered at 1500 volts remained undelaminated after 30 days implantation.

The stent can then be crimped onto a balloon of a PTCA catheter, delivered transluminally to the site of the blood vessel injury or defect and expanded into contact with the blood vessel without experiencing significant resistance to expansion from the applied metal layer. The delivery catheter can then be removed, leaving the stent of the present invention in the blood vessel.

The invention is of particular value for stents intended to carry therapeutic substances to the site of a blood vessel injury. Since many polymers suitable for carrying and delivering therapeutic substances to the lumen of the blood vessel are not themselves very blood-compatible or tissue-compatible, the metal layer according to the present invention can provide a barrier between the blood or tissue and the polymer containing the therapeutic substance. At selected sites along the stent, the metal layer can then be perforated (e.g. by mechanical or laser processes) to allow the therapeutic substances to be released to the vessel lumen or to the bloodstream.

Additional thromboresistance can be imparted to the surface of the device by applying an anti-thrombotic material as a coating over the thin metal layer. Thus, for example, heparin could be coated onto the metal layer or attached to the metal layer by methods which are well known to those skilled in the art. This could be of particular benefit for devices which are associated with a vascular injury since an injury to the blood vessel at the time of implantation could exacerbate the tendency for thrombosis during the period immediately following device implantation.

Figure 2:
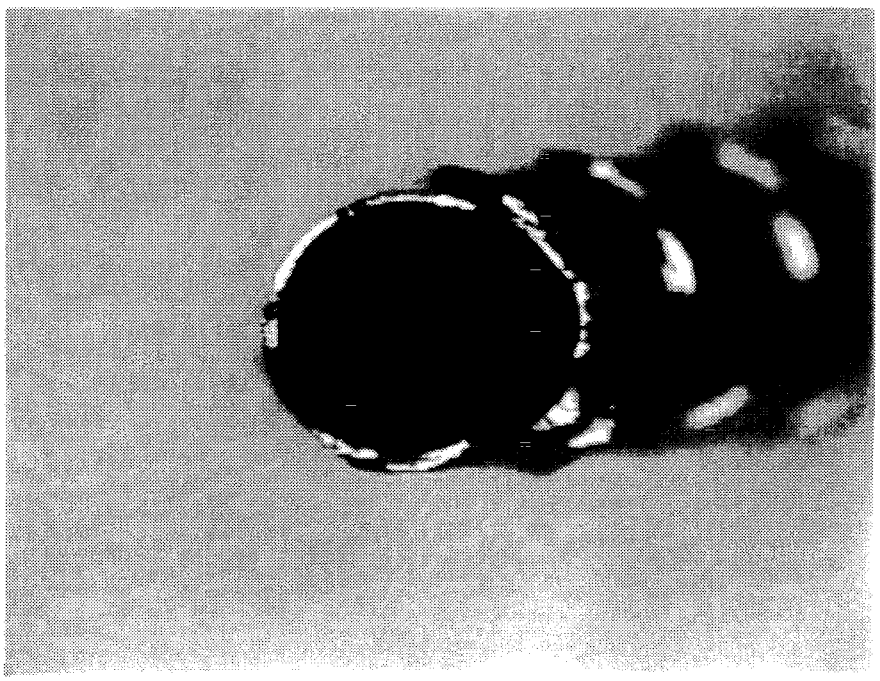
FIG. 2 is a photograph showing and end view of the stent of FIG. 1.
Figure 3:
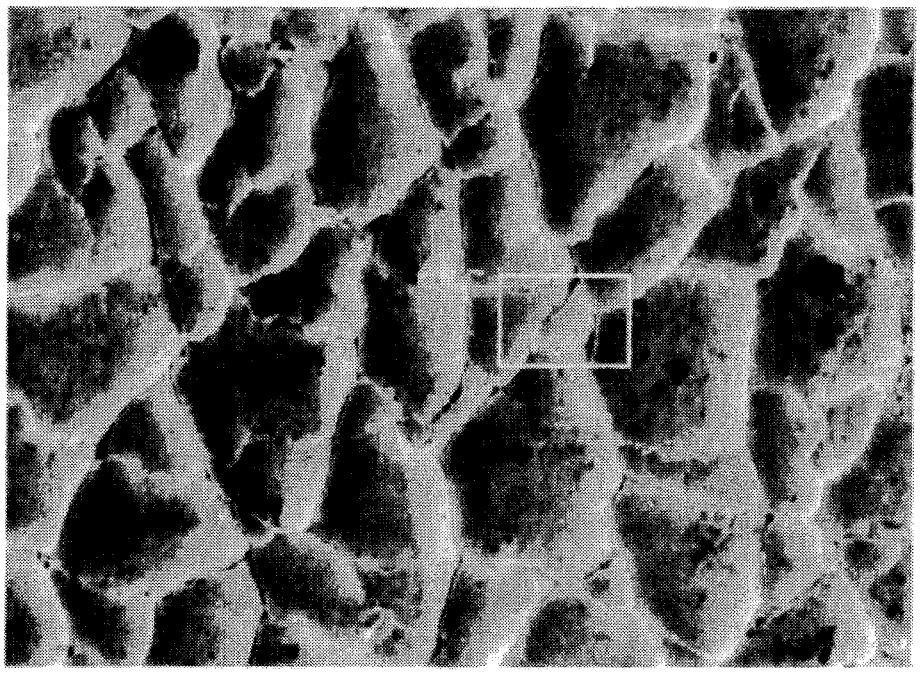
FIG. 3 is a photograph of the surface of a polymeric surface having a thin metal layer according to the present invention made by scanning electron microscope at a magnification of 650×.
Figure 4:
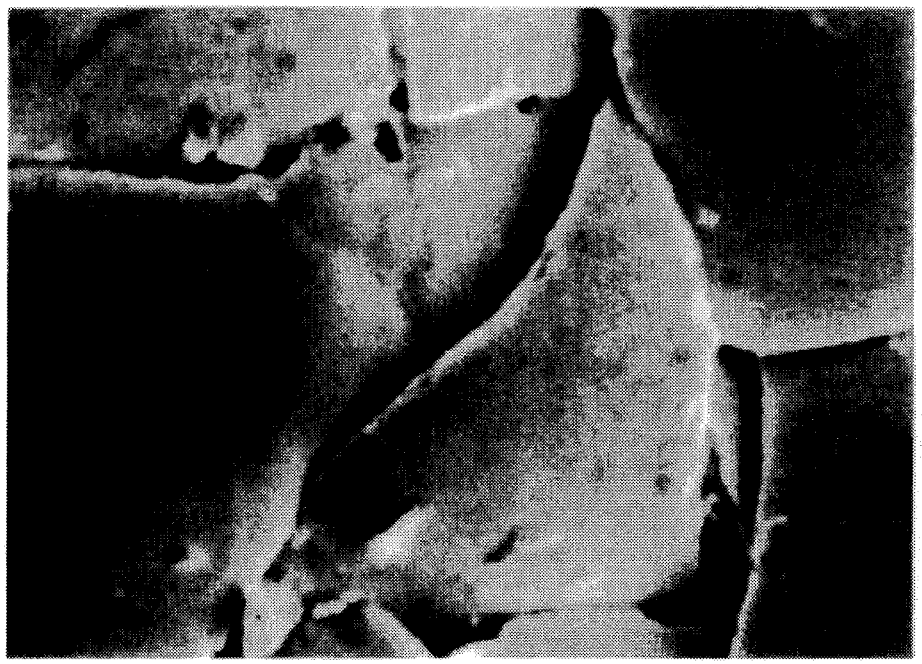
FIG. 4 is a photograph of the indicated portion of the surface of FIG. 1 at a magnification of 5000×.

Referring now to the drawings, FIGS. 1 and 2 are photographs of a stent having a tantalum metal layer according to the present invention which has been applied by sputtering the tissue-contacting surfaces of the stent. FIGS. 3 and 4 are photographs taken by a scanning electron microscope at a magnification of 650× and 5000× respectively of the surface of a silicone having a tantalum metal layer which has been applied by ion beam assisted deposition. Domains of metal separated by microscopic cracks are present. The presence of these microscopic cracks is not believed to affect the tissue or blood compatibility of the metal layer.

The following examples are illustrative of how the invention can be carried into practice.

EXAMPLES 1–3

Thin walled silicone tubes were prepared from solution. A 13% solution of silicone elastomer (SILASTIC™ Q7-4735) in xylene was prepared and placed in a glass tube. Three PTFE mandrels having an outside diameter of 0.090 inch were cleaned in a fluorocarbon solvent. The mandrels were suspended from a ring stand and dipped into the silicone solution in the glass tube. Three layers were applied at 10 minute intervals. The silicone films were then allowed to air dry on the mandrels. After several days, the films were further cured in an oven at 145° C. for 30 minutes. After cooling, the silicone tubes were stripped off the mandrels. The silicone tubes were then fixtured for a sputtering process in which a tantalum layer was to be applied to the tubes. In Example 1, a seven inch section of an everted silicone tube was threaded onto a 0.072 inch diameter fluoropolymer mandrel resulting in a loose fit of the tube on the mandrel. In Example 2, eight 20 mm sections of tubing were threaded onto 0.005 inch stainless steel wire wrapped around a 0.055 inch wire support. In Example 3, a 2.5 inch section of tubing was provided with no internal support. The samples of Examples 1–3 were then coated with high purity tantalum by radio frequency diode sputter deposition on an R. D. Mathis model SP600 sputtering machine to a thickness of about 750–1000 angstroms. Power levels for a six inch diameter tantalum target were 60 to 90 watts with target biases of 1000–1200 volts. The temperature in the vacuum chamber was approximately 100° C.

EXAMPLE 4

Four of the 20 mm tantalum sputtered tubes from Example 2 were everted by placing them over a 0.072 inch diameter fluoropolymer mandrel. One end was turned back on itself, then pulled the length of the film, thus causing the tantalum sputtered outer surface to become the inner surface. No flaking or other manifestation of delamination of the tantalum coating was observed. The everted tubes were placed inside 2.5 mm inside diameter Wiktor stents (i.e. a tantalum metal wire stent substantially as disclosed in U.S. Pat. No. 4,886,062). Some longitudinal wrinkling of the tubes occurred since the stents were slightly too small to fully accommodate the tubes. In Example 4, one stent was placed on the balloon of a 2.5 mm PRIME™ balloon catheter and the balloon was inflated to 3.0 atmospheres and held at that pressure. The stent expanded slightly causing the wrinkles in the film to disappear. A 13% solution of SILAS-TIC™ Q7-4735 in xylene was applied to the outer surface of the stent and dispersed so that all stent wires were covered. The stent was first allowed to air dry for two hours and was then transferred to a 50° C. oven overnight while still mounted on the pressurized balloon catheter. The stent was removed from the balloon catheter, slipped over a 0.072 inch diameter mandrel and placed in a 145° C. oven to cure for 30 minutes.

EXAMPLE 5

Stents were made for in vivo animal testing by placing a polymeric film stripe on a stent and applying a sputtered tantalum layer to the polymeric film. A 5% solution of poly(hydroxybutyrate-co-valerate) (PHBV) was made in dichloromethane. Approximately 3ml of the PHBV solution was pipetted onto each of two weighing dishes. Five Wiktor stents were placed into each of the two dishes and the dishes were covered with inverted petri dishes to slow drying. The excess film was then trimmed from the stent and the stent was sputter coated with tantalum substantially as in Example 1 to a tantalum thickness of about 750–1200 angstroms. Selected stents were applied to a balloon catheter and delivered by a conventional stent implantation procedure into porcine coronary arteries. At 28 days following the implantation, the arteries were sectioned. Three of four stents showed no thrombosis, inflammatory response or neointimal proliferation. On the fourth stent, the metal layer was observed to have delaminated from the polymer and thick neointima was associated with the polymer. However, there was virtually no tissue inflammation observed around the residual metal layer.

EXAMPLE 6

Stents were made as in Example 5 by placing a polymeric film stripe on a stent and applying a sputtered tantalum layer to the polymeric film. Tantalum Wiktor stents were placed on cylindrical fluoropolymer mandrels by threading the mandril through the lumen of the stent. Mandrels were sized so that the stent (0.076 inch or 0.100 inch in diameter) fit snugly against the outer surface. A solution of 20% LYCRA® polyetherurethane (Dupont) in dimethylacetamide was painted onto one side of the stents with a brush to make a stripe about 2 mm wide and 2-3 times the thickness of the stent wires. When the stripe had dried to a film, the stents were placed into a 90° C. oven overnight and then placed into a vacuum oven for 24 hours to complete the drying process. The resulting stents were then sputter coated with tantalum substantially as in Example 1 to a tantalum thickness of about 750–1200 angstroms. Five stents were implanted as in Example 5. One stent on which the metal did not delaminate was substantially free of thrombus, inflammatory response and neointimal proliferation. On four stents the metal was observed to have delaminated from the polymer and thick neointima was associated with the polymer. However, there was virtually no tissue inflammation observed around the residual metal layer.

EXAMPLE 7

Additional stents were prepared essentially as stated in Example 1 except that the tubing was sent to Spire Corporation, Bedford, Mass. for Ion Beam Assisted Deposition of tantalum onto the tubing surfaces. Microscopic examination of the tubing surface revealed that the tantalum layer had a large number of micro-cracks due to the difference in elasticity between the tantalum coating and the underlying silicone film. However, it was also noted that the adherence of the tantalum to the silicone film surface was unaffected by the cracking. SILASTIC™ medical adhesive was used to bond the film to the stent.

It will be appreciated by those skilled in the art that while the invention has been described above in connection with particular embodiments and examples, the invention is not necessarily so limited and that numerous other embodiments, examples, uses, modifications and departures from the embodiments, examples and uses may be made without departing from the inventive concepts.

We claim:

1. An indwelling intravascular device for implantation in a blood vessel of a patient over an extended period of time, said intravascular device having at least one tissue-contacting surface, the tissue-contacting surface subject to contact with a wall of the blood vessel, the tissue-contacting surface comprising a base material and a thin layer of a metal from Group VB of the Periodic Table adherent to the base material.

2. An indwelling intravascular device according to claim 1 wherein the base material is a polymer.

3. An indwelling intravascular device according to claim 2 wherein the base polymer is an elastomer.

4. An indwelling intravascular device according to claim 1 wherein the metal layer is less than about 3000 angstroms thick.

5. An indwelling intravascular device according to claim 1 wherein the metal is selected from the group consisting of tantalum and niobium.

6. An indwelling intravascular device according to claim 1 wherein the intravascular device is selected from the group consisting of a vascular prosthesis, an artificial heart valve, an electrical lead, and a catheter.

7. A vascular prosthesis for implantation in a blood vessel of a patient over an extended period of time, said vascular prosthesis having at least one tissue-contacting surface subject to contact with a wall of the blood vessel and one blood-contacting surface, the tissue-contacting surface comprising a base material and a thin layer of a metal from Group VB of the Periodic Table adherent to the base material.

8. A vascular prosthesis according to claim 7 wherein the base material is a polymer.

9. A vascular prosthesis according to claim 8 wherein the base polymer is an elastomer.

10. A vascular prosthesis according to claim 7 wherein the metal layer is less than about 3000 angstroms thick.

11. A vascular prosthesis according to claim 7 wherein the metal is selected from the group consisting of tantalum and niobium.

12. A vascular prosthesis according to claim 7 wherein the blood-contacting surface comprises a base material and a thin layer of a metal from Group VB of the Periodic Table adherent to the base material.

13. A vascular prosthesis according to claim 7 or 12 wherein the vascular prosthesis is selected from the group consisting of a vascular graft and an intravascular stent.

* * * * *